(12) United States Patent
Okaichi et al.

(10) Patent No.: US 7,868,207 B2
(45) Date of Patent: Jan. 11, 2011

(54) PROCESS FOR PRODUCING 1-(3,4-DICHLOROBENZYL)-5-OCTYLBIGUANIDE OR A SALT THEREOF

(75) Inventors: Yoshihiko Okaichi, Tokushima (JP); Nobuhito Tada, Tokushima (JP); Daisuke Nomi, Tokushima (JP); Nobuhisa Fujita, Tokushima (JP); Koichi Tsuji, Tokushima (JP); Taizo Yamaguchi, Tokushima (JP); Yasuaki Muguruma, Tokushima (JP); Hisayuki Tsujimori, Saga (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 141 days.

(21) Appl. No.: 12/439,481

(22) PCT Filed: Aug. 28, 2007

(86) PCT No.: PCT/JP2007/067107

§ 371 (c)(1),
(2), (4) Date: Feb. 27, 2009

(87) PCT Pub. No.: WO2008/026757

PCT Pub. Date: Mar. 6, 2008

(65) Prior Publication Data

US 2009/0270653 A1    Oct. 29, 2009

(30) Foreign Application Priority Data

Aug. 30, 2006  (JP) .............................. 2006-232922

(51) Int. Cl.
*C07C 277/00* (2006.01)
(52) U.S. Cl. ...................................... 564/234
(58) Field of Classification Search .................. 564/234
See application file for complete search history.

(56) References Cited

FOREIGN PATENT DOCUMENTS

| EP | 0 507 317 A2 | 10/1992 |
|----|--------------|---------|
| EP | 1 634 589 A1 | 3/2006 |
| JP | 5-194361 | 8/1993 |

OTHER PUBLICATIONS

Tsubouchi et al., "Synthesis and Structure-Activity Relationships of Novel Antiseptics", Bioorganic & Medicinal Chemistry Letters, vol. 7, No. 13, pp. 1721-1724, (1997).

*Primary Examiner*—Jafar Parsa
(74) *Attorney, Agent, or Firm*—Finnegan, Henderson, Farabow, Garrett & Dunner, L.L.P.

(57) ABSTRACT

The present invention provides a process for producing 1-(3,4-dichlorobenzyl)-5-octylbiguanide or a salt thereof, the process comprising reacting 1-cyano-3-octylguanidine or a salt thereof, with 3,4-dichlorobenzylamine or a salt thereof, in an ester-based organic solvent. According to the present invention, the reaction can be carried out at a low temperature using general-purpose equipment, and 1-(3,4-dichlorobenzyl)-5-octylbiguanide or a salt thereof can be produced in a high yield by a safe and easy process.

7 Claims, No Drawings

PROCESS FOR PRODUCING 1-(3,4-DICHLOROBENZYL)-5-OCTYLBIGUANIDE OR A SALT THEREOF

TECHNICAL FIELD

The present invention relates to a process for producing 1-(3,4-dichlorobenzyl)-5-octylbiguanide or a salt thereof.

BACKGROUND ART 1-(3,4-Dichlorobenzyl)-5-octylbiguanide represented by Formula (1)

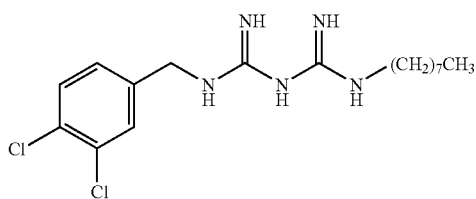

(hereinafter sometimes referred to simply as "Compound A") and salts thereof are compounds with high antimicrobial activity. Therefore, microbicides containing these compounds as active ingredients are being studied.

Compound A has heretofore been produced by the process disclosed in Japanese Unexamined Patent Publication No. H5-194361.

Specifically, the publication discloses a process in which a compound represented by Formula (2)

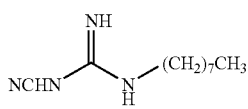

is reacted with a compound represented by Formula (3)

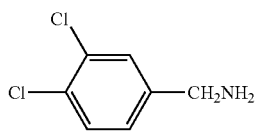

to produce Compound A.

In the process disclosed in the publication, the reaction of Compound (2) with Compound (3) is carried out in the presence or absence of a solvent such as 2-ethoxyethanol, 2-methoxyethanol, o-dichlorobenzene, mesitylene, or the like.

However, of the above solvents, 2-ethoxyethanol, 2-methoxyethanol, and o-dichlorobenzene have undesirable properties, such as positivity in chromosome tests, mutagenicity, teratogenicity, etc., and are not suitable as solvents for use in the production of medicines. o-Dichlorobenzene also has the problem of a high boiling point. 2-Ethoxyethanol, 2-methoxyethanol, and o-dichlorobenzene cannot therefore be used in the industrial production of Compound A. Thus, in the above publication, of the above solvents, only mesitylene is specifically used in the Examples.

Example 1 of the above publication specifically describes a process in which Compound (2) and a hydrochloride of Compound (3) are heated under reflux using mesitylene as a solvent, to thereby produce a monohydrochloride of Compound A. However, the yield of the process is as low as 53.1% based on Compound (2), and as low as 56.9% based on the hydrochloride of Compound (3), and is far from satisfactory. Further, since the reaction is carried out at the boiling point of mesitylene, i.e., at a high temperature of 162 to 164° C., a special heater is necessary, and it is very difficult to perform the reaction on an industrial scale using general-purpose equipment.

Thus, the above-mentioned known process is not capable of producing Compound A on an industrial scale.

DISCLOSURE OF THE INVENTION

Problems to be Solved by the Invention

An object of the present invention is to provide a safe and easy process for producing Compound A or a salt thereof in a high yield with a high purity, the process making it possible to perform a reaction at a low temperature in a short period using general-purpose equipment.

Means for Solving the Problems

To achieve the above object, the present inventors conducted extensive research on a safe and easy process for producing Compound A or a salt thereof. One idea for avoiding the need for a special heater is to employ a low-boiling-point solvent, but various low-boiling-point solvents were used and it was found that they were unable to improve the yield of Compound A or a salt thereof. The present inventors conducted further research on low-boiling-point solvents, and found that the above object can be achieved only when using specific ester-based organic solvents. The present invention has been accomplished based on these findings.

The present invention provides a process for producing 1-(3,4-dichlorobenzyl)-5-octylbiguanide or a salt thereof, as shown in the following Items 1 to 7.

Item 1. A process for producing 1-(3,4-dichlorobenzyl)-5-octylbiguanide represented by Formula (1)

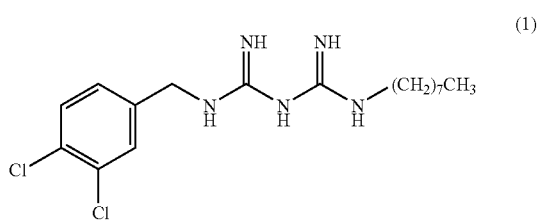

or a salt thereof, the process comprising reacting 1-cyano-3-octylguanidine represented by Formula (2)

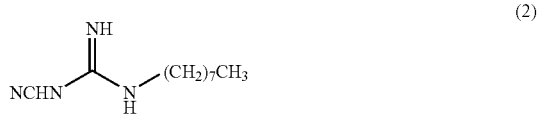

or a salt thereof, with 3,4-dichlorobenzylamine represented by Formula (3)

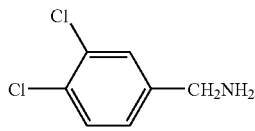
(3)

or a salt thereof, in an ester-based organic solvent.

Item 2. The process according to Item 1, wherein the ester-based organic solvent is at least one solvent selected from the group consisting of n-butyl acetate, isobutyl acetate, sec-butyl acetate, tert-butyl acetate, n-pentyl acetate, isopentyl acetate, and n-propyl propionate.

Item 3. The process according to Item 2, wherein the ester-based organic solvent is n-butyl acetate.

Item 4. The process according to any one of Items 1 to 3, wherein the reaction is carried out in the presence of an acid.

Item 5. The process according to Item 4, wherein the acid is at least one member selected from the group consisting of hydrochloric acid, sulfuric acid, phosphoric acid, and hydrobromic acid.

Item 6. The process for producing 1-(3,4-dichlorobenzyl)-5-octylbiguanide represented by Formula (1)

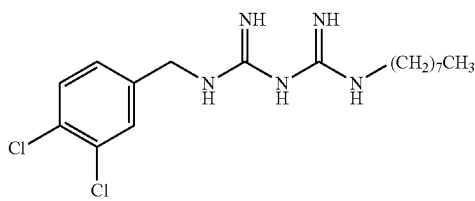
(1)

or a salt thereof, the process comprising the steps of reacting n-octylamine represented by Formula (4)

H$_2$N—(CH$_2$)$_7$CH$_3$ (4)

or a salt thereof, with a compound represented by Formula (5)

M-N(CN)$_2$ (5)

wherein M is an alkali metal, or a salt thereof, in an ester-based organic solvent to obtain 1-cyano-3-octylguanidine represented by Formula (2)

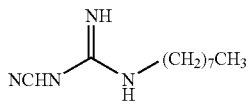
(2)

or a salt thereof; and reacting the 1-cyano-3-octylguanidine or salt thereof obtained in the above step with 3,4-dichlorobenzylamine represented by Formula (3)

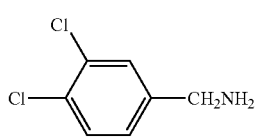
(3)

or a salt thereof, in an ester-based organic solvent.

Item 7. A process for producing 1-(3,4-dichlorobenzyl)-5-octylbiguanide represented by Formula (1)

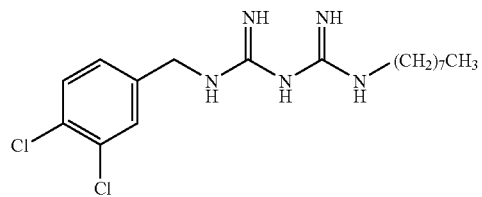
(1)

or a salt thereof, the process comprising reacting n-octylamine represented by Formula (4)

H$_2$N—(CH$_2$)$_7$CH$_3$ (4)

or a salt thereof, with a compound represented by Formula (5)

M-N(CN)$_2$ (5)

wherein M is an alkali metal, or a salt thereof, in an ester-based organic solvent to form 1-cyano-3-octylguanidine represented by Formula (2)

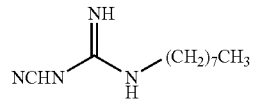
(2)

or a salt thereof; and subsequently, without isolating the 1-cyano-3-octylguanidine or salt thereof, adding 3,4-dichlorobenzylamine represented by Formula (3)

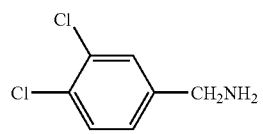
(3)

or a salt thereof, to the reaction mixture to thereby react the 1-cyano-3-octylguanidine or salt thereof with the 3,4-dichlorobenzylamine or salt thereof.

The process for producing 1-(3,4-dichlorobenzyl)-5-octylbiguanide or a salt thereof according to the present invention is described below.

Reaction Formula-1

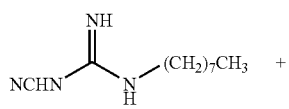
(2)

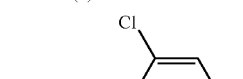
(3)

-continued

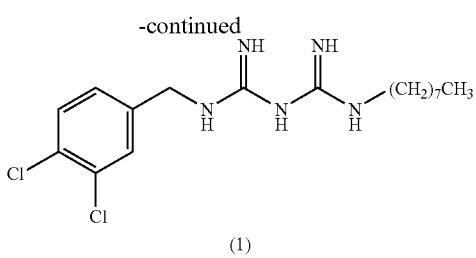

(1)

A compound (1) or a salt thereof can be obtained by allowing a compound (2) or a salt thereof to react with a compound (3) or a salt thereof in an ester-based organic solvent.

For example, propyl acetate, n-butyl acetate, isobutyl acetate, sec-butyl acetate, tert-butyl acetate, n-pentyl acetate, isopentyl acetate, n-propyl propionate, diethyl carbonate, etc., can be mentioned, as the ester-based organic solvent used in this reaction.

Among the above, ester-based organic solvents having a boiling point of around 100 to 140° C. are preferable.

Moreover, carboxylate ester is preferable as a type of ester-based organic solvent.

Mentioned as preferable examples of carboxylate esters for the method of the present invention are carboxylate esters represented by Formula (6)

$$R^1COOR^2 \qquad (6)$$

wherein $R^1$ represents $C_{1-3}$ alkyl groups and $R^2$ represents $C_{4-6}$ alkyl groups. Specific examples of the carboxylate esters represented by Formula (6) include n-butyl acetate, isobutyl acetate, sec-butyl acetate, tert-butyl acetate, n-pentyl acetate, isopentyl acetate, n-propyl propionate, etc., and n-butyl acetate is more preferable. By the use of the carboxylate esters, the compound (1) can be prepared in considerably higher yield.

In the reaction above, the compound (3) is used in an amount of usually 0.5 to 1.5 mol, preferably 0.8 to 1.1 mol, and more preferably 0.9 to 1.0 mol, per mol of the compound (2).

The amount of ester-based organic solvent is usually 2 to 20 ml, preferably 3 to 10 ml, and more preferably 5 to 8 ml per g of the compound (2).

When the compound (3) is in the form of a salt (an acid salt), it is preferable to not allow the presence of an acid in the reaction system.

When the compound (3) is in a free form, it is preferable to allow the presence of an acid in the reaction system.

The acid amount is 0.5 to 1.5 equivalent, and preferably 0.8 to 1 equivalent per equivalent of the compound (3).

Examples of acids include inorganic acids, such as hydrochloric acid, hydrobromic acid, hydroiodic acid, sulfuric acid, nitric acid, phosphoric acid, etc.; organic acids, such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethane sulfonic acid, p-toluenesulfonic acid, glutamic acid, etc.; or a mixture of the above-mentioned organic acids and the above-mentioned inorganic acids. Preferable among the above are inorganic acids, such as hydrochloric acid, hydrobromic acid, hydroiodic acid, sulfuric acid, nitric acid, phosphoric acid, etc., and hydrochloric acid is more preferable.

This reaction is carried out while being warmed, and is usually carried out at about 50 to 150° C., and preferably about 100 to 140° C. The reaction is usually completed in about 0.5 to 15 hours.

The compound that is intended to be obtained according to Reaction Formula (1) above can be separated and purified by, for example, cooling the reaction mixture, and separating a crude reaction product by a separation procedure, such as filtration, concentration, extraction, etc., and purifying the separated product by a common purification procedure, such as column chromatography, recrystallization, etc.

When the salt of the compound (1) is formed as a crystal, it is preferable to purify the salt of the compound by the following recrystallization procedure, thereby increasing the purity of the intended product. The recrystallization procedure is performed using a recrystallization solvent. For example, water, an organic solvent, or a mixture of water and an organic solvent can used as the recrystallization solvent. Organic solvents compatible with water are suitable. As specific examples of such organic solvents, acetone, tetrahydrofuran, dioxane, 1,2-dimethoxy ethane, acetonitrile, dimethylsulfoxide (DMSO), N,N-dimethyl formamide (DMF) in addition to alcohols (e.g., methanol, ethanol, 1-propanol, isopropanol, 1-butanol, isobutanol, etc.), etc., can be mentioned.

Specifically, the recrystallization procedure is performed by adding the salt of the compound (1) to a solvent, heating the resultant mixture while stirring to reach the boiling point of the recrystallization solvent to thereby dissolve the salt of the compound (1), and cooling the obtained solution to a predetermined temperature to deposit the crystals.

The crystals thus deposited were separated by filtration, centrifugal separation, etc., and, as required, the result was washed with a small amount of cold solvent, followed by drying, yielding the intended compound in a purified condition.

In the above-described recrystallization procedure, the preset temperature for depositing crystals in the cooling process is not limited. Using 15% ethanol as an example, a 15% ethanol solution of the salt of the compound (1) is cooled preferably to around 40° C. or lower, more preferably 0 to 35° C., and still more preferably 10 to 30° C. By cooling to a temperature in the above-mentioned range, the intended compound can be obtained with high purity.

Moreover, when the salt of the compound (1) is hydrochloride, the above-described recrystallization procedure is preferably carried out using, as a recrystallization solvent, a mixed solvent of water with alcohol, such as ethanol, isopropanol, etc.

Furthermore, when the salt of the compound (1) obtained according to the method of Reaction Formula-1 above is formed as dihydrochloride crystals, the crystals easily become monohydrochloride by treating, such as stirring or the like, the crystals in water or a mixed solvent of water and an organic solvent.

More specifically, the dihydrochloride of the compound (1) in the solvent was heated while stirring to reach the boiling point of the solvent for dissolution. Thereafter, the obtained solution was cooled to deposit crystals, and the crystals were separated by filtration, centrifugal separation, etc., followed by drying, yielding the monohydrochloride of the compound (1).

There is no limitation on temperatures in the cooling process of the above-described procedure, and for example, the solution of dihydrochloride of the compound (1) resulting from the heating treatment above is preferably cooled to around 40° C., more preferably 0 to 35° C., and still more preferably 10 to 30° C.

Moreover, the monohydrochloride of the compound (1) can also be obtained by treating, such as stirring or the like, the dihydrochloride of the compound (1) in the solvent in a suspended condition without causing the dihydrochloride of the compound (1) to dissolve by heating, and separating the crystals by filtration, centrifugal separation, etc., followed by drying.

In this case, a suspension of the dihydrochloride of the compound (1) is stirred, usually at around 40° C. or lower, preferably around 0 to 35° C., and still more preferably 10 to 35° C., but is not limited thereto.

A preferable method for obtaining the monohydrochloride of the compound (1) from the dihydrochloride of the compound (1) is to stir the dihydrochloride of the compound (1) in water of 10 to 35° C. without causing the dihydrochloride of the compound (1) to dissolve by heating.

Organic solvents compatible with water are preferably used in this process. Specific examples of such organic solvents include acetone, tetrahydrofuran, dioxane, 1,2-dimethoxy ethane, acetonitrile, dimethylsulfoxide (DMSO), N,N-dimethyl formamide (DMF) etc., in addition to alcohols (e.g., methanol, ethanol, 1-propanol, isopropanol, 1-butanol, isobutanol, etc.).

When a hydrate is added to the monohydrochloride of the compound (1) obtained by the above-described process, the result easily become an anhydrate by treating, such as stirring or the like, the same at 0 to 60° C., and preferably 30 to 50° C. for 0.5 to 4 hours, and preferably 1 to 2 hours in an aqueous alcohol solution comprising alcohol, such as ethanol, isopropanol, etc., in a proportion of 15% or more, and preferably 30% or more. More specifically, a monohydrochloride.1/2 hydrate of the compound (1) is subjected to a treatment such as stirring or the like at 30 to 50° C. in an aqueous ethanol solution comprising 30% or more of ethanol for about 2 hours to yield a monohydrochloride-anhydrate of the compound (1). In the case of an aqueous ethanol solution comprising 15% of ethanol, a monohydrochloride-anhydrate of the compound (1) can be obtained by a treatment, such as stirring or the like, at 40 to 60° C. or higher for about 2 hours.

In the present invention, a compound represented by Formula (2) for use as a starting material is prepared by the method shown below, as an example.

Reaction Formula-2

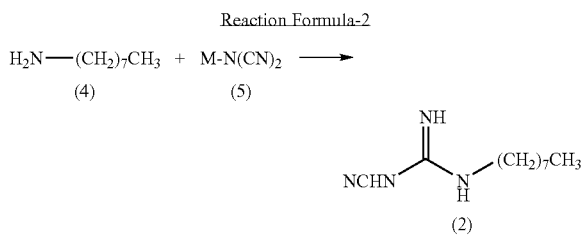

wherein, M is an alkali metal.

Compound (2) or a salt thereof can be obtained by allowing a compound represented by Formula (4) (hereinafter sometimes referred to simply as "Compound (4)") or a salt thereof to react with a compound represented by Formula (5) (hereinafter sometimes referred to simply as "Compound (5)") or a salt thereof.

As a suitable alkali metal of Compound (5), lithium, sodium, potassium, etc., can be mentioned.

This reaction is carried out in an inactive solvent or without a solvent. Examples of an inactive solvent for use in this reaction include water; aromatic hydrocarbon organic solvents, such as benzene, toluene, xylene, etc.; ether organic solvents, such as diethylether, tetrahydrofuran, dioxane, monoglyme, diglyme, etc.; halogenated hydrocarbon organic solvents, such as dichloromethane, dichloroethane, chloroform, carbon tetrachloride, etc.; lower alcohol organic solvents, such as methanol, ethanol, isopropanol, butanol, tert-butanol, ethylene glycol, etc.; fatty acid organic solvents, such as acetic acid, etc.; ester-based organic solvents, such as ethyl acetate, propyl acetate, n-butyl acetate, isobutyl acetate, sec-butyl acetate, tert-butyl acetate, n-pentyl acetate, isopentyl acetate, n-propyl propionate, diethyl carbonate, etc.; ketone organic solvents, such as acetone, methyl ethyl ketone, etc.; acetonitrile, pyridine, DMF, DMSO, hexamethylphosphoric triamide, or a mixed solvent thereof, etc.

When Compound (4) is in the form of a salt (an acid salt), it is preferable to not allow the presence of an acid in the reaction system.

When Compound (4) is in a free form, it is preferable to allow the presence of an acid in the reaction system.

The acid amount is 0.5 to 1.5 equivalents, and preferably 0.8 to 1 equivalents per equivalent of Compound (4).

Examples of acids include inorganic acids, such as hydrochloric acid, hydrobromic acid, hydroiodic acid, sulfuric acid, nitric acid, phosphoric acid, etc.; organic acids, such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethane sulfonic acid, p-toluenesulfonic acid, glutamic acid, etc.; or a mixture of the above-mentioned inorganic acids and the above-mentioned organic acids. Preferable among the above are inorganic acids, such as hydrochloric acid, hydrobromic acid, hydroiodic acid, sulfuric acid, nitric acid, phosphoric acid, etc., and hydrochloric acid is more preferable.

When using the aforementioned solvent, the amount thereof is usually 5 to 20 ml, preferably 8 to 12 ml, and more preferably 9 to 11 ml per equivalent of 1 g of Compound (4).

This reaction is usually carried out at about 50 to 150° C., and preferably about 70 to 130° C. The reaction is usually completed in about 0.5 to 40 hours.

By performing the reaction of the above-mentioned Compound (4) or a salt thereof with Compound (5) or a salt thereof in an ester-based organic solvent, the synthetic reaction of Compound (2) represented by the above-mentioned Reaction Formula-2 and the reaction of the above-mentioned Reaction Formula-1 using Compound (2) as the starting material can be performed continuously. Accordingly, a series of these reaction processes can be carried out without isolating Compound (2) or a salt thereof as an intermediate, thus resulting in a significant yield improvement.

The starting material compounds used in the above reaction formulas may be suitable salts, and the desired compounds obtained by the above reactions may be in the form of suitable salts.

Suitable salts are pharmaceutically acceptable salts including, for example, metal salts such as alkali metal salts (e.g., sodium salt, potassium salt, etc.), alkaline earth metal salts (e.g., calcium salt, magnesium salt, etc.), etc., ammonium salts, alkali metal carbonates (e.g., lithium carbonate, potassium carbonate, sodium carbonate, cesium carbonate, etc.), alkali metal hydrogencarbonates (e.g., lithium hydrogencarbonate, sodium hydrogencarbonate, potassium hydrogencarbonate, etc.), alkali metal hydroxides (e.g., lithium hydroxide, sodium hydroxide, potassium hydroxide, cesium hydroxide, etc.), and other salts of inorganic bases; tri(lower) alkylamines (e.g., trimethylamine, triethylamine, N-ethyldiisopropylamine, etc.), pyridine, quinoline, piperidine, imidazole, picoline, dimethylaminopyridine, dimethylaniline, N-(lower)alkylmorpholines (e.g., N-methylmorpholine and the like), 1,5-diazabicyclo[4.3.0]nonene-5(DBN), 1,8-diazabicyclo[5.4.0]undecene-7(DBU), 1,4-diazabicyclo[2.2.2]octane (DABCO), and other salts of organic bases; hydrochlorides, hydrobromides, hydroiodides, sulfates, nitrates, phosphates, and other salts of inorganic acids; formic acid, acetates, propionates, oxalates, malonates, succinates, fumarates, maleates, lactates, malates, citrates, tartrates, carbonates, picrates, methanesulfonates, ethanesulfonates, p-toluenesulfonates, glutamates, and other salts of organic acids; etc.

The starting materials and desired compound shown in each Reaction Formula include solvates thereof (e.g., hydrates, ethanolates, etc.). Preferable solvates include hydrates. The desired compound obtained according to Reaction Formula (2) above can be separated and purified from the reaction mixture by, for example, cooling the reaction mixture, separating the crude reaction product from the reaction mixture by a separation procedure such as filtration, concentration, extraction and/or other separation procedures, and then purifying the crude reaction product by column chromatography, recrystallization and/or another conventional purification procedure.

Effects of the Invention

According to the present invention, even though a reaction is carried out at a low temperature using general-purpose equipment without the need of a special heater, the desired compound, 1-(3,4-dichlorobenzyl)-5-octylbiguanide or a salt thereof, can be produced in a short reaction time, by a safe and simple process, and in a high yield. The present invention is also advantageous in that the use of an ester-based organic solvent makes it possible to carry out the reaction of Compound (4) with Compound (5) to synthesize Compound (2), and the reaction of Compound (2) with Compound (3) to synthesize Compound (1), in the same solvent and in the same reactor. Further, since the process of the present invention produces substantially no by-products, 1-(3,4-dichlorobenzyl)-5-octylbiguanide or a salt thereof with a higher purity can be obtained by performing an easy purification procedure.

BEST MODE FOR CARRYING OUT THE INVENTION

Reference Examples, Examples and Comparative Examples are given below to illustrate the present invention in further detail.

Reference Example 1

1-cyano-3-n-octylguanidine

A 7.00-kg quantity of Compound (4) (54.16 mol) was dissolved in 105 liters of ethyl acetate, and the resulting mixture was cooled to 5° C. or below. A 2.66-kg quantity of concentrated sulfuric acid (27.12 mol) was added thereto dropwise at a temperature of 40° C. or below while stirring. To the thus-obtained suspension of 1/2 sulfate of Compound (4) was added 5.06 kg of sodium dicyanamide (56.83 mol), and the resulting suspension was heated under reflux for 7 hours. The reaction solution was cooled to 40° C. or below, and 70 liters of water was added thereto. Subsequently, the resulting solution was heated to 80 to 90° C. (internal temperature) to distill the ethyl acetate off. The remaining liquid was cooled to 40° C. or below, and 70 liters of toluene was then added thereto, followed by the extraction of 1-cyano-3-n-octyl guanidine at about 50° C. The extracted toluene layer was washed with 35 liters of water at about 50° C. and cooled to 10° C. or below, followed by stirring for about 30 minutes. The resulting precipitated crystals were separated and washed with 7 liters of toluene. The resulting crystals were dried at 40° C. for 7.5 hours, yielding 1-cyano-3-n-octylguanidine.

Yield: 9.11 kg (The yield was 85.7% based on the Compound (4).) White crystals having a melting point of 69 to 74° C. (no clear melting point was observed)

IR(KBr) spectrum: 3439, 3296, 2916, 2164, 1659, 1556, 1160, 718, and 572 cm$^{-1}$ Thermogravimetric measurement/differential thermal analysis: 73.5° C. (weak), an endothermic peak at 77.5° C.

$^1$H-NMR (CDCl$_3$) spectrum: 0.88 ppm (t, J=6.6 Hz, 3H), 1.20-1.38 ppm (m, 10H), 1.43-1.62 ppm (m, 2H), 3.17 ppm (dd, J=6.9 Hz, J=6.0 Hz, 2H), 5.60-5.70 ppm (bs, 2H), 5.80-5.95 ppm (bs, 1H)

Reference Example 2

Acidolysis of 1-(3,4-dichlorobenzyl)-5-octylbiguanide dihydrochloride

A 1-g quantity of 1-(3,4-dichlorobenzyl)-5-octyl biguanide dihydrochloride was dissolved in 15 ml of 10% ethanol, followed by refluxing for 5 hours. HPLC analysis was conducted under the conditions described below.

The yield of 1-[N-(3,4-dichlorobenzyl)carbamoyl-3-octyl]guanidine (holding time: 9.84 minutes) was 0.91%, and the yield of 1-(N-octyl-carbamoyl)-3-(3,4-dichlorobenzyl)guanidine (holding time: 10.54 minutes) was 0.22%.

HPLC Analysis Conditions:
Column: YMC AM302 4.6 mm I.D.×150 mm
Eluate: MeCN/0.05 M aqueous solution of sodium 1-octanesulfonate/acetic acid=700/300/1
Detector: UV 254 nm The physical property values of the resulting 1-[N-(3,4-dichlorobenzyl)carbamoyl-3-octyl]guanidine were as follows:

NMR (DMSO-d$_6$) δ: 0.86 (3H, t, J=6.0 Hz), 1.07-1.35 (10H, m), 1.35-1.49 (2H, m), 2.95-3.15 (2H, m), 4.12 (2H, d, J=6.3 Hz), 6.78-7.40 (4H, m), 7.23 (1H, dd, J=2.1 Hz, J=8.4 Hz), 7.46 (1H, d, J=2.1 Hz), 7.54 (1H, d, J=8.4 Hz)

The physical property values of the resulting 1-(N-octyl-carbamoyl)-3-(3,4-dichlorobenzyl)guanidine were as follows:

NMR (DMSO-d$_6$) δ: 0.85 (3H, t, J=6.6 Hz), 1.02-1.40 (12H, m), 2.89-2.95 (2H, m), 4.33 (2H, bs), 5.76-7.00 (4H, m), 7.28 (1H, dd, J=2.1 Hz, J=8.1 Hz), 7.52 (1H, d, J=2.1 Hz), 7.58 (1H, d, J=8.1 Hz)

Example 1

1-(3,4-dichlorobenzyl)-5-octylbiguanide monohydrochloride 1/2 hydrate

A 9.82-g quantity of Compound (2) (0.05 mol) and 10.63 g of 3,4-dichlorobenzylamine (0.05 mol) were added to 49 ml of butyl acetate, followed by refluxing for 6 hours. The reaction solution was concentrated under reduced pressure, and a mixture of 12 ml of water and 47 ml of isopropyl alcohol was added and dissolved into the remainder. To the thus-obtained solution was added, dropwise, 10.13 g of concentrated hydrochloric acid. The resulting mixture was stirred at 28 to 30° C. for 30 minutes, and the precipitated crystals were then filtered out. The thus-obtained crystals were washed with a small amount of isopropyl alcohol, yielding 23.42 g of (non-dried) 1-(3,4-dichlorobenzyl)-5-octylbiguanide dihydrochloride. The resulting crystals were suspended in 167 ml of water without drying, the suspension was then stirred at 25 to 27° C. for 2 hours, followed by separation of the crystals by filtration. The thus-obtained crystals were washed with a small amount of water and dried at 40° C. for 20 hours, yielding 17.05 g of 1-(3,4-dichlorobenzyl)-5-octyl biguanide monohydrochloride 1/2 hydrate having a purity of 99.9% at a yield of 81.6%.

Example 2

1-(3,4-dichlorobenzyl)-5-octylbiguanide dihydrochloride

A 100-g quantity of Compound (4) (0.774 mol) was dissolved in 1 liter of n-butyl acetate, and 37.6 g of concentrated sulfuric acid (0.383 mol) was added thereto while stirring. To the thus-obtained suspension of 1/2 sulfate of Compound (4) was added 68.9 g of sodium dicyanamide (0.774 mol), and the resulting suspension was heated under reflux for 3 hours. The reaction solution was cooled to about 20° C., and the organic layer thereof was sequentially washed with about 500 ml each of (i) 5% hydrochloric acid, (ii) 5% aqueous caustic soda solution, (iii) 5% aqueous sodium bicarbonate solution, and (iv) water.

To the thus-obtained n-butyl acetate solution of Compound (2) were added 118.5 g of Compound (3) (0.673 mol) and then 58.4 ml of concentrated hydrochloric acid while stirring. The reaction solution was heated, and about 800 ml of n-butyl acetate was distilled off under atmospheric pressure (ordinary pressure), followed by heating the reaction solution under reflux for 3.5 hours. Subsequently, the reaction solution was cooled to about 40° C., and 900 ml of isopropanol, 100 ml of water, and 134 ml of concentrated hydrochloric acid were added thereto. The mixture was stirred at 60 to 70° C. for 1 hour and cooled to 10° C. or below and the precipitated crystals were then separated. The resulting crystals were washed with 200 ml of isopropanol and dried at 60° C., yielding 1-(3,4-dichlorobenzyl)-5-octylbiguanide dihydrochloride.

Yield: 243.8 g (The yield was 81.3% based on the Compound (3).)

Melting point: 228.9° C.

IR(KBr) spectrum: 2920, 1682, 1634, 1337, 1035, 820, and 640 cm$^{-1}$

Example 3

1-(3,4-dichlorobenzyl)-5-octylbiguanide monohydrochloride 1/2H$_2$O

A 100-g quantity of dihydrochloride of Compound A (0.225 mol) was added to 1 liter of 15% aqueous isopropanol solution, and the resulting mixture was heated until the Compound A was dissolved. The thus-obtained solution was cooled to about 35° C., and 0.2 g of seed crystals was added thereto, followed by stirring at 25 to 35° C. for 1 hour. The solution after stirring was cooled to 10° C. or below, and the precipitated crystals were then separated. The precipitated crystals were washed with 200 ml of water, yielding wet crystals.

After recrystallizing the wet crystals from 1 liter of 15% aqueous isopropanol solution, the resulting crystals were dried at 40° C., yielding crude crystals of 1-(3,4-dichlorobenzyl)-5-octylbiguanide monohydrochloride 1/2H$_2$O.

Yield: 90.54 g (The yield was 96.5% based on the dihydrochloride of Compound A.)

Purity (HPLC) of 99.9% or higher

Particle size: The object can be met as long as the crystals can pass through an 870-μm sieve.

Melting point: 173 to 174° C.

$^1$H-NMR (DMSO-d$_6$) spectrum: 0.85 ppm (t, J=6.8 Hz, 3H), 1.10-1.50 ppm (m, 12H), 2.92-3.08 ppm (m, 2H), 4.33 ppm (d, J=6.3 Hz, 2H), 6.80-7.20 ppm (bs, 3H), 7.30 ppm (d, J=8.4 Hz, 1H), 7.48-7.62 ppm (m, 3H), 7.70-7.90 ppm (bs, 0.5H)

IR(KBr) spectrum: 3316, 3190, 2928, 1584, 1549, 1152, 1032, and 723 cm$^{-1}$

Thermogravimetric measurement/differential thermal analysis: Three endothermic peaks were observed around 40±10° C., 90±10° C., and 170±5° C. Temperatures at the endothermic peaks differed slightly between lots; however, three distinctive peaks were observed.

Powder X-ray diffraction spectrum (2θ): 3.6°, 7.2°, 10.9°, 18.1°, and 25.5°

Example 4

1-(3,4-dichlorobenzyl)-5-octylbiguanide monohydrochloride 1/2H$_2$O

An 8.92-kg quantity of the crude crystals of dihydrochloride of Compound A was added to 15% aqueous ethanol solution (a mixture of 114 liters of purified water and 20 liters of ethanol), and the resulting mixture was heated until the crude crystals were dissolved. The thus-obtained solution was cooled to about 40° C., and 90 g of seed crystals was added thereto, followed by stirring at 30 to 40° C. for about 2 hours. The solution after stirring was cooled to about 10° C., and the precipitated crystals were subjected to centrifugal separation. The resulting crystals were dried at 40° C., yielding 1-(3,4-dichlorobenzyl)-5-octyl biguanide monohydrochloride 1/2H$_2$O.

Yield: 8.15 kg (The yield was 97.4% based on crude crystals of dihydrochloride of Compound A.)

Purity (HPLC) of 99.6% or higher

Melting point: 173-174° C.

$^1$H-NMR (DMSO-d$_6$) spectrum: 0.85 ppm (t, J=6.8 Hz, 3H), 1.10-1.50 ppm (m, 12H), 2.92-3.08 ppm (m, 2H), 4.33 ppm (d, J=6.3 Hz, 2H), 6.80-7.20 ppm (bs, 3H), 7.30 ppm (d, J=8.4 Hz, 1H), 7.48-7.62 ppm (m, 3H), 7.70-7.90 ppm (bs, 0.5H)

IR(KBr) spectrum: 3316, 3190, 2928, 1584, 1549, 1152, 1032, and 723 cm$^{-1}$

Thermogravimetric measurement/differential thermal analysis: Three endothermic peaks were observed around 40±10° C., 90±10° C., and 170±5° C. Temperatures at the endothermic peaks differed slightly between lots; however, three distinctive peaks were observed.

Powder X-ray diffraction spectrum (2θ): 3.6°, 7.2°, 10.9°, 18.1°, and 25.5°

Example 5

1-(3,4-dichlorobenzyl)-5-octylbiguanide monohydrochloride 1/2H$_2$O

A 9-kg quantity of Compound (4) (69.64 mol) was dissolved in 90 liters of n-butyl acetate and then cooled to 10° C.

or below. To the resulting solution was added 3.35 kg of concentrated sulfuric acid (34.16 mol) while stirring at a temperature not exceeding 40° C. (about 4 minutes).

To the thus-obtained suspension of 1/2 sulfate of Compound (4) was added 6.2 kg (69.64 mol) of sodium dicyanamide, followed by heating under reflux for about 3 hours. The resulting reaction solution was cooled to about 20 to 40° C., and the organic layer thereof was sequentially washed with about 45 liters each of (i) 5% aqueous caustic soda solution, (ii) 5% hydrochloric acid, (iii) 5% aqueous sodium bicarbonate solution, and (iv) 5% aqueous saline solution.

The thus-obtained n-butyl acetate solution of Compound (2) was cooled to about 15° C., and 11.6 kg of Compound (3) (65.89 mol) and 6.7 kg of concentrated hydrochloric acid were sequentially added thereto while stirring at a temperature not exceeding 35° C. While heating the solution under reflux, about 72 liters of the solvent was distilled off over about 6.5 hours. The reaction solution was cooled to about 80° C., and 72 liters of isopropanol and 18 kg of purified water were added thereto. The reaction solution was then heated while stirring at about 60° C. until the once-deposited crystals redissolved. A 14.1-kg quantity of concentrated hydrochloric acid was added thereto at a temperature of about 44 to 55° C., and the mixture was stirred for 1 hour without heating. The resulting mixture was cooled to 10° C. or below, and the precipitated crystals were then separated. The resulting crystals were suspended in 54 liters of isopropanol, and the resulting suspension was stirred at 10° C. or below for about 1 hour, followed by separation of the crystals. The thus-obtained crystals (dihydrochloride) were added to 225 liters of purified water without drying, and the mixture was stirred at 25 to 35° C. for about 2 hours, followed by separation of the crystals. The resulting crystals were washed with 45 liters of purified water and subjected to vacuum drying (15 mmHg) at about 40° C. using a conical dryer, yielding crude crystals of 1-(3, 4-dichlorobenzyl)-5-octylbiguanide monohydrochloride 1/2$H_2O$.

Yield: 21.26 kg (The yield was 77.2% based on Compound (3).)

Example 6

Purification Method

A 19.0-kg quantity of the crude crystals of monohydrochloride 1/2$H_2O$ of Compound A was added to a 15% aqueous ethanol solution (a mixture of 179 liters of purified water and 32 liters of ethanol), and the resulting mixture was heated (at a temperature of 80° C. or below) until the crude crystals were dissolved, followed by filtration under heating. The filtrate was refluxed again so as to confirm complete dissolution of the crude crystals and then cooled to about 35° C. Subsequently, 76 g of seed crystals were added thereto, and the mixture was cooled to 20° C. over 1 hour and then cooled to 10° C. over 30 minutes. The precipitated crystals were subjected to centrifugal separation and washed with 42 liters of purified water in a separator. The resulting crystals were dried at 40° C. over 22 hours, yielding the monohydrochloride 1/2$H_2O$ of Compound A.

Yield: 18.34 kg (The yield was 96.5% based on the crude crystals of monohydrochloride 1/2$H_2O$ of Compound A.)

Purity (HPLC) 99.9% or higher

Particle size: The object can be met as long as the crystals can pass through an 870-μm sieve.

Melting point: 173-174° C.

$^1$H-NMR (DMSO-$d_6$) spectrum: 0.85 ppm (t, J=6.8 Hz, 3H), 1.10-1.50 ppm (m, 12H), 2.92-3.08 ppm (m, 2H), 4.33 ppm (d, J=6.3 Hz, 2H), 6.80-7.20 ppm (bs, 3H), 7.30 ppm (d, J=8.4 Hz, 1H), 7.48-7.62 ppm (m, 3H), 7.70-7.90 ppm (bs, 0.5H)

IR(KBr) spectrum: 3316, 3190, 2928, 1584, 1549, 1152, 1032, and 723 $cm^{-1}$

Thermogravimetric measurement/differential thermal analysis: Three endothermic peaks were observed around 40±10° C., 90±10° C., and 170±5° C. Temperatures at the endothermic peaks differed slightly between lots; however, three distinctive peaks were observed.

Powder X-ray diffraction spectrum (2θ): 3.6°, 7.2°, 10.9°, 18.1°, and 25.5°

Example 7

1-(3,4-dichlorobenzyl)-5-octylbiguanide monohydrochloride

An examination was conducted to determine how the concentration and temperature of an aqueous ethanol solution affect the transfer of monohydrochloride 1/2$H_2O$ of Compound A into an anhydrate (Form I crystal). The monohydrochloride 1/2$H_2O$ of Compound A was suspended in an aqueous ethanol solution having a concentration of 30% or higher, and its transformation into a Form I crystal was completed within 2 hours from the initiation of the reaction at 30° C. At 25° C., the formation of a Form I crystal was observed from 2 hours after the initiation of the reaction, and the transformation into a Form I crystal was completed 4 hours after. At 20° C., the formation of a Form I crystal was observed from 2 hours after the initiation of the reaction, but the transformation into a Form I crystal was not completed even after 6 hours.

The same examination was conducted using a 15% aqueous ethanol solution. At 35° C., the formation of a Form I crystal was observed from 4 hours after the initiation of the reaction at 35° C., and at 40° C., the transformation into a Form I crystal was completed within 2 hours. When a 10% aqueous ethanol solution was used, the transformation into a Form I crystal was not completed even after 6 hours even though the temperature was raised to 57° C.

From the above examination, it became clear that the monohydrochloride 1/2$H_2O$ of Compound A can be completely transformed into a Form I crystal if it is suspended in an aqueous ethanol solution having a concentration of 30% or higher and the resulting suspension is stirred at a temperature within the range of 30° C. to 45° C. for 2 hors or more. It also became clear that when the monohydrochloride 1/2$H_2O$ of Compound A is suspended in a 15% aqueous ethanol solution, the transformation into a Form I crystal can be completed by stirring the resulting suspension at 40° C. for 2 hours or more.

(Form I crystal):

Melting point: 177-179° C.

Powder X-ray diffraction spectrum (2θ): 3.9°, 17.5°, 21.9°, and 22.5°

Comparative Example 1

1-(3,4-dichlorobenzyl)-5-octylbiguanide monohydrochloride

A 200-ml quantity of mesitylene was added to 20 g of Compound (2) and 20.2 g of hydrochloride of Compound (3), followed by heating for 1.5 hours under reflux. After completion of the reaction, the reaction solution was returned to room temperature and then mesitylene was removed therefrom. A 200-ml quantity of 10% aqueous ethanol solution was added to the residue. The resulting mixture was heated and sequentially washed with 10% ethanol solution, water, and isopropyl ether, yielding 28.1 g of crude product. The resulting crude product was subjected to recrystallization using ethyl acetate, yielding 22.1 g of 1-(3,4-dichlorobenzyl)-5-octylbiguanide monohydrochloride in the form of a white prismatic crystal.

The yields were 53.1% based on Compound (2) and 56.9% based on Compound (3).

Comparative Example 2

1-(3,4-dichlorobenzyl)-5-octylbiguanide monohydrochloride

The crude product (4 g) obtained in Comparative Example 1 were dissolved in 60 ml of 15% EtOH while heating and then cooled to 40° C., followed by stirring at the same temperature for 4 hours. The deposited crystals were filtered out, yielding 3.6 g of 1-(3,4-dichlorobenzyl)-5-octyl biguanide monohydrochloride. The yield was 90% based on crude product.

Melting point: White crystals, melting point 169-170° C.

IR(KBr) spectrum: 3314, 3176, 2920, 1595, 1545, 1146, 1027, and 723 cm$^{-1}$

Thermogravimetric measurement/differential thermal analysis: Two strong endothermic peaks were observed around 110±5° C. and 170±5° C. Temperatures at the endothermic peaks differed slightly between lots; however, two distinctive peaks were observed.

Comparative Example 3

Toluene Used as a Reaction Solvent

To 15 ml of toluene were added 1 g of octylamine hydrochloride (6.0 mmol) and 0.56 g of NaN(CN)$_2$ (6.3 mmol), followed by refluxing for 2 hours. To the resulting mixture was added 1.2 g of 3,4-dichlorobenzyl amine (5.7 mmol), followed by additional refluxing for 2.5 hours. The resulting reaction mixture was subjected to HPLC analysis. The resulting mixture contained, in addition to 1-(3,4-dichlorobenzyl)-5-octyl biguanide monohydrochloride (5.85 minutes, 55%), 1,5-dioctyl biguanide (11.40 minutes, 9%), 1,5-bis(3,4-dichlorobenzyl)biguanide (3.46 minutes, 6%), 1-(3,4-dichlorobenzyl)-3-cyanoguanidine (2.1 minutes, 4%), and 1-octyl-3-cyanoguanidine (2.60 minutes, 11%).

Conditions for HPLC Analysis:

Column YMCAM302 4.6 mm I.D.×150 mm No. 188

Eluate: MeCN/0.05 M aqueous solution of sodium 1-octanesulfonate/acetic acid=700/300/1

Detector: UV 254 nm

The invention claimed is:

1. A process for producing 1-(3,4-dichlorobenzyl)-5-octylbiguanide represented by Formula (1)

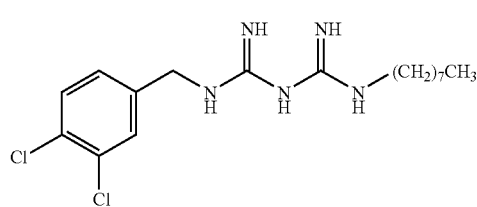

or a salt thereof, the process comprising reacting 1-cyano-3-octylguanidine represented by Formula (2)

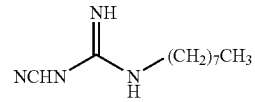

or a salt thereof, with 3,4-dichlorobenzylamine represented by Formula (3)

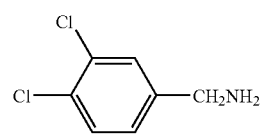

or a salt thereof, in an ester-based organic solvent.

2. The process according to claim 1, wherein the ester-based organic solvent is at least one solvent selected from the group consisting of n-butyl acetate, isobutyl acetate, sec-butyl acetate, tert-butyl acetate, n-pentyl acetate, isopentyl acetate, and n-propyl propionate.

3. The process according to claim 2, wherein the ester-based organic solvent is n-butyl acetate.

4. The process according to any one of claims 1 to 3, wherein the reaction is carried out in the presence of an acid.

5. The process according to claim 4, wherein the acid is at least one member selected from the group consisting of hydrochloric acid, sulfuric acid, phosphoric acid, and hydrobromic acid.

6. The process for producing 1-(3,4-dichlorobenzyl)-5-octylbiguanide represented by Formula (1)

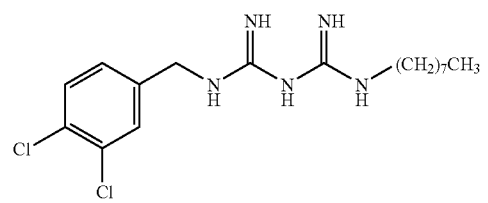

or a salt thereof, the process comprising the steps of reacting n-octylamine represented by Formula (4)

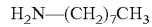

or a salt thereof, with a compound represented by Formula (5)

wherein M is an alkali metal, or a salt thereof, in an ester-based organic solvent to obtain 1-cyano-3-octylguanidine represented by Formula (2)

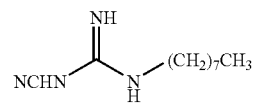

or a salt thereof; and reacting the 1-cyano-3-octylguanidine or salt thereof obtained in the above step with 3,4-dichlorobenzylamine represented by Formula (3)

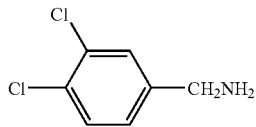   (3)

or a salt thereof, in an ester-based organic solvent.

7. A process for producing 1-(3,4-dichlorobenzyl)-5-octylbiguanide represented by Formula (1)

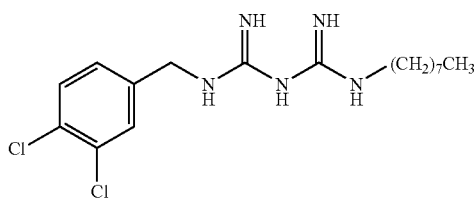   (1)

or a salt thereof, the process comprising reacting n-octylamine represented by Formula (4)

H$_2$N—(CH$_2$)$_7$CH$_3$   (4)

or a salt thereof, with a compound represented by Formula (5)

M-N(CN)$_2$   (5)

wherein M is an alkali metal, or a salt thereof, in an ester-based organic solvent to form 1-cyano-3-octylguanidine represented by Formula (2)

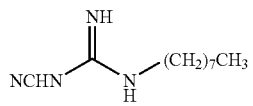   (2)

or a salt thereof; and subsequently, without isolating the 1-cyano-3-octylguanidine or salt thereof, adding 3,4-dichlorobenzylamine represented by Formula (3)

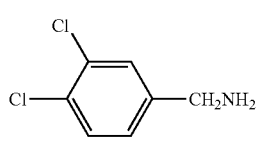   (3)

or a salt thereof, to the reaction mixture to thereby react the 1-cyano-3-octylguanidine or salt thereof with the 3,4-dichlorobenzylamine or salt thereof.

* * * * *